United States Patent
Sumida et al.

(10) Patent No.: US 9,506,042 B2
(45) Date of Patent: Nov. 29, 2016

(54) GLUCOSE DEHYDROGENASE

(71) Applicant: TOYOBO CO., LTD., Osaka-shi, Osaka (JP)

(72) Inventors: Yosuke Sumida, Tsuruga (JP); Rie Hirao, Tsuruga (JP); Yuu Utashima, Tsuruga (JP); Hiroaki Kitazawa, Tsuruga (JP); Hiroshi Aiba, Tsuruga (JP); Takahide Kishimoto, Tsuruga (JP); Shusaku Yanagidani, Tsuruga (JP)

(73) Assignee: Toyobo Co., Ltd., Osaka (JP)

( * ) Notice: Subject to any disclaimer, the term of this patent is extended or adjusted under 35 U.S.C. 154(b) by 0 days.

(21) Appl. No.: 14/584,552

(22) Filed: Dec. 29, 2014

(65) Prior Publication Data

US 2015/0111280 A1    Apr. 23, 2015

Related U.S. Application Data

(63) Continuation-in-part of application No. PCT/JP2013/067309, filed on Jun. 25, 2013.

(30) Foreign Application Priority Data

Jun. 29, 2012   (JP) ................................ 2012-146803

(51) Int. Cl.

| | | |
|---|---|---|
| *C12N 9/02* | (2006.01) | |
| *C12N 9/04* | (2006.01) | |
| *C12Q 1/54* | (2006.01) | |
| *C12Q 1/32* | (2006.01) | |
| *C12Q 1/00* | (2006.01) | |
| *A61B 5/145* | (2006.01) | |

(52) U.S. Cl.
CPC ............. *C12N 9/0006* (2013.01); *C12Q 1/006* (2013.01); *C12Q 1/32* (2013.01); *C12Y 101/9901* (2013.01); *A61B 5/14532* (2013.01)

(58) Field of Classification Search
CPC . C12Q 1/32; C12N 9/006; C12Y 101/99018
USPC ..................................... 435/189, 190, 287.1
See application file for complete search history.

(56) References Cited

U.S. PATENT DOCUMENTS

| | | | |
|---|---|---|---|
| 7,514,250 | B2 | 4/2009 | Omura et al. |
| 7,662,600 | B2 | 2/2010 | Kawaminami et al. |
| 8,039,248 | B2 | 10/2011 | Kawaminami et al. |
| 8,691,547 | B2 | 4/2014 | Omura et al. |
| 2006/0063217 | A1 | 3/2006 | Omura et al. |
| 2008/0003628 | A1 | 1/2008 | Kitabayashi et al. |
| 2008/0220460 | A1 | 9/2008 | Kawaminami et al. |
| 2009/0176262 | A1 | 7/2009 | Omura et al. |
| 2009/0317848 | A1 | 12/2009 | Kawaminami et al. |
| 2010/0297743 | A1 | 11/2010 | Omura et al. |
| 2011/0318810 | A1 | 12/2011 | Tajima et al. |
| 2012/0122130 | A1 | 5/2012 | Omura et al. |
| 2012/0244565 | A1 | 9/2012 | Nishio et al. |
| 2014/0234533 | A1 | 8/2014 | Omura et al. |

FOREIGN PATENT DOCUMENTS

| | | |
|---|---|---|
| JP | 2007-289148 A | 11/2007 |
| JP | 2008-237210 A | 10/2008 |
| WO | WO 2004/058958 A1 | 7/2004 |
| WO | WO 2006/101239 A1 | 9/2006 |
| WO | WO 2008/059777 A1 | 5/2008 |
| WO | WO 2010/140431 A1 | 12/2010 |
| WO | WO 2011/068050 A1 | 6/2011 |
| WO | WO 2013/022074 A1 | 2/2013 |
| WO | WO 2013/051682 A1 | 4/2013 |
| WO | WO 2013/065623 A1 | 5/2013 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Gan et al., "Choline Dehydrogenase [Colletotrichum gloeosporioides Nara gc5]", National Center for Biotechnology Information, Protein Database [online], GenBank Database Accession No. ELA34144 (Dec. 14, 2012).
Sygmund et al., *Microbial Cell Factories*, 10: 106 (2011).
Sygmund et al., *Microbiology*, 157: 3203-3212 (2011).
Zafar et al., *Analytical Chemistry*, 84(1): 334-341 (2012).
Japanese Patent Office, International Search Report in International Patent Application No. PCT/JP2013/067309 (Jul. 23, 2013).

* cited by examiner

*Primary Examiner* — Robert Mondesi
*Assistant Examiner* — Md. Younus Meah
(74) *Attorney, Agent, or Firm* — Leydig, Voit & Mayer, Ltd.

(57) ABSTRACT

The present invention provides a novel glucose dehydrogenase that has excellent substrate specificity, specific activity, thermal stability, and the like, and that is suitable for use in SMBG sensors. The present invention provides a purified polypeptide comprising an amino acid sequence having at least 80% identity to the sequence of SEQ ID NO: 1 and having glucose dehydrogenase activity.

17 Claims, 4 Drawing Sheets

(1) Purified enzyme CsGDH (before removal of sugar chain)
(2) Purified enzyme CsGDH (after removal of sugar chain)

SEQUENCE LISTING

```
<160> NUMBER OF SEQ ID NOS: 10

<210> SEQ ID NO 1
<211> LENGTH: 635
<212> TYPE: PRT
<213> ORGANISM: Colletotrichum sp.

<400> SEQUENCE: 1
```

```
Met Pro Leu Phe Arg Gln Ser Lys Ser Gln Pro Arg Trp Pro Gly Val
1               5                   10                  15

Ala Ser Ala Val Phe Leu Ala Ala Ser Ser Val Ala Asn Ala Tyr Ala
            20                  25                  30

Ile Pro Arg Asp Ile Lys Pro Ser Glu Leu Leu Gln Ser Tyr Asp Tyr
            35                  40                  45

Val Ile Val Gly Gly Gly Thr Ala Gly Leu Thr Val Ala Asp Arg Leu
50                      55                  60

Thr Glu Asp Pro Asn Thr Thr Val Leu Val Leu Glu Ala Gly Gly Trp
65              70                  75                  80

Ser Asn Met Thr Asp Asn Leu Met Ala Tyr Val Ala Gly Arg Ser Gly
            85                  90                  95

Arg Ile Leu Trp Pro Gly Leu Gln Ser Val Pro Gln Glu His Leu Asn
            100                 105                 110

Gly Arg Thr Asn Thr Val Ser Val Ala Arg Gln Val Gly Gly Gly Ser
        115                 120                 125

Ala Ile Asn Ala Met Ile Thr Met Arg Gly Ser Ala Glu Asp Tyr Asp
        130                 135                 140

Arg Trp Ala Thr Leu Phe Gly Pro Glu Ala Gln Arg Gly Thr Ala Asp
145                 150                 155                 160

Trp Ser Trp Asp Gly Ile Leu Pro Phe Phe Lys Lys Ala Leu His Phe
                165                 170                 175

Thr Glu Pro Pro Pro Glu Leu Thr Asp Asn Phe Asp Ile Lys Tyr Asp
                180                 185                 190

Ala Ser Tyr Trp Gly Asp Ser Ser Glu Leu Tyr Ala Gly Trp Pro Arg
            195                 200                 205

Phe Tyr Tyr Pro Gly Val Thr Pro Leu Leu Glu Ala Phe Lys Glu Ile
        210                 215                 220

Glu Gly Val Glu Phe Pro Pro Asp Ser Gly Ala Gly Gln Pro Gly Val
225                 230                 235                 240

Tyr Trp Phe Pro Ala Phe Met Asp Pro Arg Thr Val Thr Arg Ser Tyr
                245                 250                 255

Ala Ala Thr Gly His Tyr Leu Asn Val Asn Ala Thr Arg Gln Asn Tyr
            260                 265                 270

His Leu Leu Ile Asn Ser Gln Ala Arg Lys Leu Ile Leu Asp Asp Asn
        275                 280                 285

Leu Thr Ala Thr Gly Val Glu Phe Pro Leu Ala Asn Asn Thr Leu Phe
        290                 295                 300

Thr Val Asn Ala Arg Lys Glu Val Ile Leu Ser Ala Gly Thr Val His
305                 310                 315                 320

Thr Pro Gln Leu Leu Gln Leu Ser Gly Val Gly Pro Lys Lys Leu Leu
                325                 330                 335

Glu Glu Ala Gly Ile Asp Val Arg Val Asp Leu Pro Gly Val Gly Gln
            340                 345                 350

Asn Phe Gln Asp His Ser Ser Leu Ser Thr Val Asn Ile Thr Leu Ser
        355                 360                 365

Lys Ile Thr Ser Ile His Pro Asn Pro Lys Asp Leu Val Asp Gly Asn
        370                 375                 380

Asp Phe Lys Thr Trp Ala Asp Glu Val Trp Gln Ala Asn Lys Thr Gly
385                 390                 395                 400

Pro Tyr Ser Ile Ser Trp Thr Asn Leu Ala Gly Trp Leu Pro Phe Thr
            405                 410                 415
```

```
Val Ile Ser Asp Lys Ala Asp Glu Leu Ala Thr Lys Leu Glu Gln Gln
                420                 425                 430

Asp Phe Ala Ser Leu Leu Pro Ala Gly Thr Asp Ala Thr Val Val Ala
            435                 440                 445

Gly Phe Glu Ala Gln Met Lys Leu Leu Ala Ala Gln Met Arg Ser Lys
        450                 455                 460

Asn Thr Ala Phe Thr Arg Tyr Gln Leu Ile Ala Glu His Gly Val Gln
465                 470                 475                 480

Gly Pro Val Gly Leu Gln Ser Phe Ser Arg Gly Thr Ile Asn Ile Asn
                485                 490                 495

Thr Thr Asn Pro Trp Asn Thr Glu Pro Val Ile Asp Tyr Arg Val Leu
                500                 505                 510

Ser Asn Pro Leu Glu Ala Asp Tyr Phe Val Glu Ser Ile Lys Phe Leu
            515                 520                 525

Arg Arg Tyr Asn Phe Glu Thr Ser Leu Ala Ser Lys Phe Glu Pro Val
        530                 535                 540

Glu Tyr Val Pro Gly Pro Asp Val Thr Ser Asp Glu Asp Leu Lys Ala
545                 550                 555                 560

Tyr Ile Ala Arg Ala Leu Ser Pro Ser Asp Tyr His Pro Val Gly Thr
                565                 570                 575

Ala Ser Met Leu Pro Leu Asn Leu Gly Gly Val Val Asp Gln Thr Leu
            580                 585                 590

Arg Val Tyr Gly Val Lys Asn Leu Arg Val Val Asp Ala Ser Val Met
        595                 600                 605

Pro Met Val Pro Gly Ala Asn Thr Cys Gln Pro Thr Tyr Ala Leu Ala
    610                 615                 620

Glu Lys Ala Ser Glu Ile Ile Lys Gln Gly Ile
625                 630                 635

<210> SEQ ID NO 2
<211> LENGTH: 1908
<212> TYPE: DNA
<213> ORGANISM: Colletotrichum sp.

<400> SEQUENCE: 2
atgcccttgt ttcgccagtc caagtcccag cctcggtggc cgggcgtcgc atccgcggtc      60
tttctcgcag cgagctctgt cgccaatgct tacgccattc cgcgtgacat caagccatct     120
gagctgctgc agagctatga ttatgtcatt gttggaggtg aacggcaggg cctgactgtc     180
gcagaccgtc tcacggagga ccctaacacg acagtcttgg tccttgaagc cggcggctgg     240
agcaacatga ctgacaacct gatggcctac gtcgcgggca gatccggcag gattctgtgg     300
cccggcctcc agtctgtgcc gcaagagcac ttgaatggaa gaaccaacac cgtctccgtt     360
gccaggcaag ttggaggcgg ctccgccata aacgccatga tcaccatgcg tggctctgca     420
gaggactatg accgctgggc gaccctgttc ggacccgagg ctcagcgggg cactgctgac     480
tggagctggg atggtatcct gccgttcttc aagaaggctc tccacttcac tgagccccct     540
cctgagctta ccgacaactt tgatatcaag tatgacgcct cctactgggg cgactcttcc     600
gagctctacg ccggttggcc ccggttctac tacccaggag tgactcccct cttgaagca      660 ttcaaggaga tcgagggcgt tgaattccct cccgacagtg gtgccggcca gcaggtgtt      720 tactggttcc ccgccttcat ggaccccgt actgtcactc gctcctacgc cgccactggt      780
cactatctca acgttaacgc gacccgccaa aactaccacc tgttgattaa cagccaggct     840
cgcaagctga tcttggacga caacctcacc gccactggag ttgagttccc cctggcaaac     900
```

```
aacaccctat tcactgtcaa cgcaaggaag gaggtcattc tctctgctgg taccgttcac      960
actcctcagc ttctgcagct gagcggtgtc ggtcccaaga agcttcttga ggaggcgggc     1020
attgacgtgc gtgttgacct tcccggtgtt ggccagaact tccaggacca tagcagtctc     1080
tccacagtga acatcactct ctccaagatt acatcgattc accccaaccc caaggacctg     1140
gtcgatggaa acgacttcaa gacctgggcc gacgaggttt ggcaagctaa caagactggc     1200
ccttactcca tctcatggac caacttggct ggctggctcc ctttcaccgt catttcggac     1260
aaggctgacg agcttgccac caagctggag caacaagact cgccagcct gctgcccgct      1320 ggcaccgacg ccacagtggt cgccggtttt gaggcgcaga tgaagctcct ggccgcccag     1380
atgcgctcca aaacacggc cttcacccgt taccagctta tcgcggagca cggcgtccag      1440
ggccccgtgg ggttgcaatc cttcagccgc ggcaccatca acatcaacac caccaacccg     1500
tggaacacgg agccggtgat cgactaccgc gtcctcagta accccctcga ggccgactac     1560
ttcgtcgagt caatcaagtt ccttcgccgc tacaacttcg agacctccct ggcctccaag     1620
tttgagccgg tcgagtacgt ccctggcccc gacgtcacct ctgatgagga cctgaaggcc     1680
tacatcgccc gtgctttgtc cccctccgac taccaccccg tgggtacagc gtccatgctg     1740
cctctgaact gggtggtgt cgttgaccag accctgcgcg tgtacggagt caagaacctg      1800
agagtcgttg acgccagtgt catgcccatg gtccccggtg ccaatacttg ccagcctacg     1860
tacgctcttg ccgagaaggc ttcggaaatc atcaagcaag catctaa                    1908
```

<210> SEQ ID NO 3
<211> LENGTH: 17
<212> TYPE: PRT
<213> ORGANISM: Colletotrichum sp.

<400> SEQUENCE: 3

Lys Gly Thr Ala Asp Trp Ser Trp Asp Gly Ile Leu Pro Phe Phe Lys
1               5                   10                  15

Lys

<210> SEQ ID NO 4
<211> LENGTH: 19
<212> TYPE: PRT
<213> ORGANISM: Colletotrichum sp.

<400> SEQUENCE: 4

Lys Tyr Asp Ala Ser Tyr Trp Gly Asp Ser Ser Glu Ile Tyr Ala Gly
1               5                   10                  15

Trp Pro Arg

<210> SEQ ID NO 5
<211> LENGTH: 30
<212> TYPE: DNA
<213> ORGANISM: Artificial Sequence
<220> FEATURE:
<223> OTHER INFORMATION: Synthetic sequence of designed polinucleotide
      described in Example

<400> SEQUENCE: 5
tgggacggsa thttgccstt cttcaagaag                                        30

<210> SEQ ID NO 6
<211> LENGTH: 30
<212> TYPE: DNA
<213> ORGANISM: Artificial Sequence

```
<220> FEATURE:
<223> OTHER INFORMATION: Synthetic sequence of designed polinucleotide
      described in Example

<400> SEQUENCE: 6
sgagtcsccc cagtasgasg cgtcgtactt                                    30

<210> SEQ ID NO 7
<211> LENGTH: 20
<212> TYPE: DNA
<213> ORGANISM: Artificial Sequence
<220> FEATURE:
<223> OTHER INFORMATION: Synthetic sequence of designed polinucleotide
      described in Example

<400> SEQUENCE: 7
gctctccact tcactgagcc                                               20

<210> SEQ ID NO 8
<211> LENGTH: 29
<212> TYPE: DNA
<213> ORGANISM: Artificial Sequence
<220> FEATURE:
<223> OTHER INFORMATION: Synthetic sequence of designed polinucleotide
      described in Example

<400> SEQUENCE: 8
ccctcctgag cttaccgaca actttgata                                     29

<210> SEQ ID NO 9
<211> LENGTH: 29
<212> TYPE: DNA
<213> ORGANISM: Artificial Sequence
<220> FEATURE:
<223> OTHER INFORMATION: Synthetic sequence of designed polinucleotide
      described in Example

<400> SEQUENCE: 9
tatcaaagtt gtcggtaagc tcaggaggg                                     29

<210> SEQ ID NO 10
<211> LENGTH: 20
<212> TYPE: DNA
<213> ORGANISM: Artificial Sequence
<220> FEATURE:
<223> OTHER INFORMATION: Synthetic sequence of designed polinucleotide
      described in Example

<400> SEQUENCE: 10
ggctcagtga agtggagagc                                               20
```

GLUCOSE DEHYDROGENASE

CROSS-REFERENCE TO RELATED APPLICATIONS

This patent application is a continuation-in-part of co-pending International Patent Application No. PCT/JP2013/067309, filed on Jun. 25, 2013, which claims the benefit of Japanese Patent Application No. 2012-146803, filed on Jun. 29, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 10,128 bytes ASCII (Text) file named "719243Sequence-Listing.txt," created Dec. 29, 2014.

TECHNICAL FIELD

The present invention relates to a glucose dehydrogenase (hereinafter also referred to as "GDH"). More specifically, the present invention relates to a flavin-bound glucose dehydrogenase (hereinafter also referred to as "FGDH"), a fungus that produces the flavin-bound glucose dehydrogenase, a method for producing the flavin-bound glucose dehydrogenase, a method for measuring glucose using the flavin-bound glucose dehydrogenase, and the like.

BACKGROUND ART

Self-monitoring of blood glucose (SMBG) is important for diabetic patients to manage their blood glucose levels and to use this monitoring in treatment. Simple blood glucose self-monitoring devices using an electrochemical biosensor have recently been widely used in SMBG. The biosensor includes an insulating substrate on which electrodes and an enzyme reaction layer are formed.

Examples of enzymes used herein include glucose dehydrogenase (GDH), glucose oxidase (GO), and the like. In terms of methods using GO (EC 1.1.3.4), a problem has been noted in that dissolved oxygen in a measurement sample is likely to affect the measurement results. Although GDH is unaffected by dissolved oxygen, it is not suitable for accurately measuring blood glucose levels, because, for example, a pyrroloquinoline quinone-dependent glucose dehydrogenase (PQQ-GDH) (EC 1.1.5.2 (formerly EC 1.1.99.17)) acts on sugars such as maltose and lactose, in addition to glucose.

A flavin adenine dinucleotide-dependent glucose dehydrogenase (hereinafter also referred to as "FADGDH") is known to be unaffected by dissolved oxygen and to have almost no action on maltose.

For example, Patent Documents 1 to 5 report enzymes derived from *Aspergillus terreus* and *Aspergillus oryzae*, and modifications of these.

Non-patent Document 1 reports an enzyme derived from *Glomerella cingulata*, which is ascomycete (asexual stage name: *Colletotricum gloeosporoides*).

These enzymes, however, have relatively high reactivity to xylose (Patent Document 1 and Non-patent Document 1), and there is therefore room for improvement in accurately measuring blood glucose of people who are undergoing a xylose tolerance test.

Further, a flavin-bound GDH having relatively low action on xylose (Patent Document 6), a modified GDH having combined advantages of GO and GDH (Patent Document 7), and the like, have recently been developed, but there is still room for improvement.

CITATION LIST

Patent Documents

Patent Document 1: WO2004/058958
Patent Document 2: WO2006/101239
Patent Document 3: JP2007-289148A
Patent Document 4: JP2008-237210A
Patent Document 5: WO2008/059777
Patent Document 6: WO2010/140431
Patent Document 7: WO2011/068050

Non-Patent Document

Non-patent-Document 1: Microbiology (2011) 157: 3203-3212

SUMMARY OF INVENTION

Technical Problem

Under the above circumstances, the present inventors conducted intensive research to develop a novel glucose dehydrogenase that is more suitable for use in SMBG, and found that the use of an enzyme having high specific activity and excellent stability, in addition to excellent substrate specificity, enables shortening the measurement time while accurately measuring blood glucose levels with a small amount of enzyme. More specifically, an object of the present invention is to provide a novel glucose dehydrogenase that has excellent substrate specificity, specific activity, thermal stability, and the like, and is thus being suitable for use in SMBG sensors.

Solution to Problem

The present inventors conducted intensive research to achieve the above object. As a result of screening many microorganisms, they found that some microorganisms that had not been reported to produce glucose dehydrogenase have glucose dehydrogenase activity. The inventors then isolated and purified this enzyme, analyzed its characteristics, and thereby found that the enzyme was a flavin-bound glucose dehydrogenase that has excellent substrate specificity, high specific activity, and excellent thermal stability.

The present inventions have been accomplished as a result of further research and improvement based on these findings. Representative examples of the present invention are described below.

Item 1. A flavin-bound glucose dehydrogenase comprising any one of the following polypeptides (a) to (c):

(a) a polypeptide having the amino acid sequence of SEQ ID NO: 1;
(b) a polypeptide having the amino acid sequence of SEQ ID NO: 1 in which one or several amino acid residues are substituted, deleted, inserted, added, and/or inverted, and having glucose dehydrogenase activity; and
(c) a polypeptide having an amino acid sequence with 80% or more identity to the amino acid sequence of SEQ ID NO: 1, and having glucose dehydrogenase activity.

Item 2: A DNA of any one of the following (A) to (F):

(A) DNA encoding the amino acid sequence of SEQ ID NO: 1;

(B) DNA having the base sequence of SEQ ID NO: 2;

(C) DNA having a base sequence with 80% or more identity to the base sequence of SEQ ID NO: 2, and encoding a polypeptide having glucose dehydrogenase activity;

(D) DNA hybridizing to a base sequence complementary to the base sequence of SEQ ID NO: 2 under stringent conditions, and encoding a polypeptide having glucose dehydrogenase activity;

(E) DNA having the base sequence of SEQ ID NO: 2 in which one or several bases are substituted, deleted, inserted, added, and/or inverted, and encoding a polypeptide having glucose dehydrogenase activity; and (F) DNA encoding a polypeptide having the amino acid sequence of SEQ ID NO: 1 in which one or several amino acid residues are substituted, deleted, inserted, added, or inverted, and having glucose dehydrogenase activity.

Item 3. A vector containing the DNA of Item 2.

Item 4. A transformant containing the vector of Item 3.

Item 5. A method for producing the flavin-bound glucose dehydrogenase of Item 1, the method comprising:

culturing a microorganism containing the DNA of Item 2; and purifying the obtained culture medium.

Item 6. The method for producing the flavin-bound glucose dehydrogenase of Item 5, the method comprising:

culturing the transformant of Item 4; and purifying the obtained culture medium.

Item 6. A method for measuring a glucose concentration, the method comprising causing the flavin-bound glucose dehydrogenase of Item 1 to act on glucose.

Item 7. A glucose assay kit comprising the flavin-bound glucose dehydrogenase of Item 1.

Item 8. A glucose sensor comprising the flavin-bound glucose dehydrogenase of Item 1.

Item A1. A purified polypeptide comprising an amino acid sequence having at least 80% identity to the sequence of SEQ ID NO: 1 and having glucose dehydrogenase activity.

Item A2. The purified polypeptide of Item A1, wherein the amino acid sequence having at least 80% identity to the sequence of SEQ ID NO: 1 has at least 85% identity to the sequence of SEQ ID NO: 1.

Item A3. The purified polypeptide of Item A1, wherein the amino acid sequence having at least 80% identity to the sequence of SEQ ID NO: 1 has at least 88% identity to the sequence of SEQ ID NO: 1.

Item A4. The purified polypeptide of Item A1, wherein the amino acid sequence having at least 80% identity to the sequence of SEQ ID NO: 1 has at least 90% identity to the sequence of SEQ ID NO: 1.

Item A5. The purified polypeptide of Item A1, wherein the amino acid sequence having at least 80% identity to the sequence of SEQ ID NO: 1 has at least 93% identity to the sequence of SEQ ID NO: 1.

Item A6. The purified polypeptide of Item A1, wherein the amino acid sequence having at least 80% identity to the sequence of SEQ ID NO: 1 has at least 95% identity to the sequence of SEQ ID NO: 1.

Item A7. The purified polypeptide of Item A1, wherein the amino acid sequence having at least 80% identity to the sequence of SEQ ID NO: 1 has at least 98% identity to the sequence of SEQ ID NO: 1.

Item A8. The purified polypeptide of Item A1, wherein the amino acid sequence having at least 80% identity to the sequence of SEQ ID NO: 1 has at least 99% identity to the sequence of SEQ ID NO: 1.

Item A9. The purified polypeptide of Item A1, wherein the polypeptide does not comprise the amino acid sequence of SEQ ID NO: 1.

Item A10. A polypeptide comprising an amino acid sequence having at least 80% identity to the sequence of SEQ ID NO: 1, wherein the polypeptide has glucose dehydrogenase activity, and wherein the polypeptide is obtained by recombinantly expressing a DNA encoding the polypeptide.

Item A11. The polypeptide of Item A10, wherein the recombinant expression comprises:

preparing a recombinant vector comprising the DNA, introducing the recombinant vector into a cell, and cultivating the cell.

Item A12. The polypeptide of Item A11, wherein the cell is not *Colletotrichum* RD056779 strain.

Item A13. The polypeptide of Item A11, wherein the cell is at least one cell selected from the group consisting of *Escherichia coli, Bacillus subtilis*, yeast, an insect cell, an animal cell, a plant cell, and an animal cell.

Item A14. The polypeptide of Item A10, wherein the amino acid sequence having at least 80% identity to the sequence of SEQ ID NO: 1 has at least 85% identity to the sequence of SEQ ID NO: 1.

Item A15. The polypeptide of Item A10, wherein the amino acid sequence having at least 80% identity to the sequence of SEQ ID NO: 1 has at least 88% identity to the sequence of SEQ ID NO: 1.

Item A16. The polypeptide of Item A10, wherein the amino acid sequence having at least 80% identity to the sequence of SEQ ID NO: 1 has at least 90% identity to the sequence of SEQ ID NO: 1.

Item A17. The polypeptide of Item A10, wherein the amino acid sequence having at least 80% identity to the sequence of SEQ ID NO: 1 has at least 93% identity to the sequence of SEQ ID NO: 1.

Item A18. The polypeptide of Item A10, wherein the amino acid sequence having at least 80% identity to the sequence of SEQ ID NO: 1 has at least 95% identity to the sequence of SEQ ID NO: 1.

Item A19. The polypeptide of Item A10, wherein the amino acid sequence having at least 80% identity to the sequence of SEQ ID NO: 1 has at least 98% identity to the sequence of SEQ ID NO: 1.

Item A20. The polypeptide of Item A10, wherein the amino acid sequence having at least 80% identity to the sequence of SEQ ID NO: 1 has at least 99% identity to the sequence of SEQ ID NO: 1.

Advantageous Effects of Invention

The flavin-bound glucose dehydrogenase (FGDH) of the present invention has significantly reduced reactivity to maltose, D-galactose, and D-xylose; therefore, even when D-glucose and these sugars are present together in a sample, the amount and the concentration of glucose can be accurately measured. Further, the FGDH of the present invention has excellent thermal stability and thus enables production of efficient sensor strips, which involves heat treatment. Also, the FGDH of the present invention is stable within a wide pH range, and thus it can be suitably used under a wide range of conditions. With these characteristics, the FGDH of the present invention makes it possible to accurately measure the glucose concentration in any sample containing D-glucose (e.g., blood and food (such as seasonings and beverages)).

DESCRIPTION OF EMBODIMENTS

Figure 1:
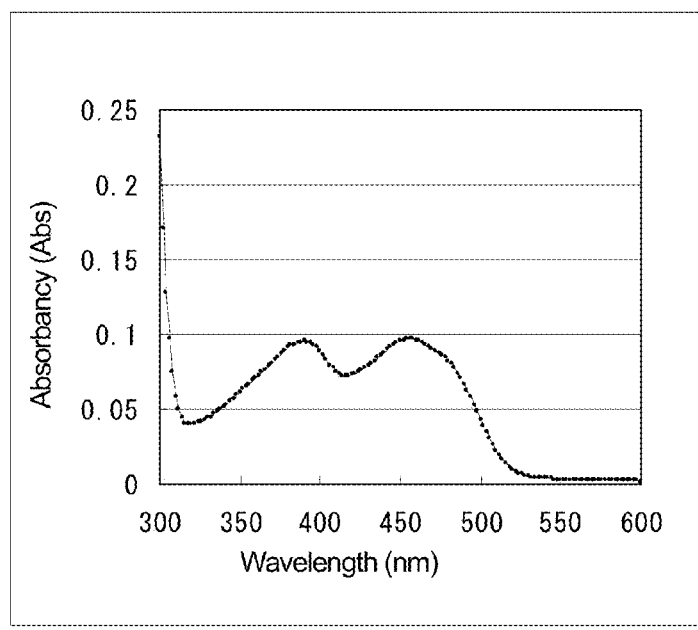
FIG. 1 is a graph showing the absorption spectrum of RD056779-derived GDH.

The present invention is described below in detail.
1. Flavin-Bound Glucose Dehydrogenase (FGDH)
1-1. Glucose Dehydrogenase Activity A glucose dehydrogenase (GDH) is an enzyme that has a physicochemical property of catalyzing a reaction in which hydroxy groups of glucose are oxidized to produce glucono-δ-lactone in the presence of an electron acceptor. In this specification, this physicochemical property represents glucose dehydrogenase activity, and the terms "enzyme activity" and "activity" represent this enzyme activity unless otherwise noted. The electron acceptor is not limited as long as it can accept electrons in a reaction catalyzed by GDH. For example, 2,6-dichlorophenolindophenol (DCPIP), phenazine methosulfate (PMS), 1-methoxy-5-methylphenazium methylsulfate, and ferricyanide compounds may be used.

Various methods are known for measuring glucose dehydrogenase activity. A method used in this specification is a method using DCPIP as an electron acceptor and measuring the activity based on the change in absorbance of a sample at a wavelength of 750 nm before and after the reaction. The following are the specific reagent composition and measurement conditions unless otherwise noted.
Method for Measuring Glucose Dehydrogenase Activity
Reagent
150 mM phosphate buffer solution containing 1.5 M D-glucose, pH of 7.0 (containing 0.1% Triton X-100)
3.1 mM 2,6-dichlorophenolindophenol (DCPIP) solution The reaction reagent is obtained by mixing 20 mL of the phosphate buffer solution containing D-glucose and 10 mL of the DCPIP solution.
Measurement Conditions The reaction reagent (3 mL) is preheated at 37° C. for 5 minutes. A GDH solution (0.1 mL) is added and gently mixed. Water is used as a control, and changes in absorbance at 750 nm are recorded for 5 minutes by using a spectrophotometer at a controlled temperature of 37° C. Based on the linear portion (i.e., after the reaction rate becomes constant), the change in absorbance per minute ($\Delta OD_{TEST}$) is measured. In a blind test, a solvent used for dissolving GDH is added to the reagent mixture in place of the GDH solution, and the change in absorbance per minute ($\Delta OD_{BLANK}$) is measured in a similar manner. Based on the obtained values, the GDH activity is determined by the following equation. Here, one unit (U) of the GDH activity is equal to the enzyme amount that reduces 1 μmol of DCPIP in 1 minute in the presence of D-glucose at a concentration of 1 M.

$$\text{Activity (U/mL)} = \{-(\Delta OD_{TEST} - \Delta OD_{BLANK}) \times 3.1 \times \text{dilution rate}\}/\{0.85 \times 0.1 \times 1.0\}$$

In the equation, 3.1 is the total liquid amount (mL) of the reaction reagent and the enzyme solution, 0.85 is the millimolar extinction coefficient ($cm^2/\mu mol$) under conditions in which the activity is measured, 0.1 is the amount (mL) of the enzyme solution, and 1.0 is the optical path length (cm) of the cell. In this specification, the enzyme activity is measured according to the above measurement method unless otherwise indicated.

The GDH of the present invention refers to flavin-bound GDH (FGDH), which requires flavin as a prosthetic group.

The FGDH of the present invention is preferably isolated FGDH or purified FGDH. The FGDH of the present invention may be in a state of being dissolved in a solution described above that is suitable for storage or in a freeze-dried state (e.g., powder). The expression "isolated" used in regard to the enzyme (FGDH) of the present invention refers to a state in which the enzyme is substantially free of components (e.g., host-cell-derived contaminating proteins, other components, and culture media) other than the enzyme. Specifically, for example, the isolated enzyme of the present invention contains contaminating proteins in an amount of less than about 20%, preferably less than about 10%, more preferably less than about 5%, even more preferably less than about 1%, of the total (by weight). It is also possible for the FGDH of the present invention to be present in a solution (e.g., buffer) suitable for storage or for measurement of enzyme activity.
1-2. Polypeptide The FGDH of the present invention preferably comprises any one of the following polypeptides (a) to (c):
(a) a polypeptide having the amino acid sequence of SEQ ID NO: 1;
(b) a polypeptide having the amino acid sequence of SEQ ID NO: 1 in which one or several amino acid residues are substituted, deleted, inserted, and/or added, and having glucose dehydrogenase activity; and
(c) a polypeptide having an amino acid sequence with 80% or more identity to the amino acid sequence of SEQ ID NO: 1, and having glucose dehydrogenase activity.

As shown in Example 5, the amino acid sequence of SEQ ID NO: 1 is equal to the amino acid sequence of FGDH derived from *Colletotrichum* RD056779 (hereinafter also referred to as "CsGDH"). The FGDH derived from *Colletotrichum* RD056779 exhibits all the characteristics described in Sections 1-3 to 1-9 below.

The polypeptide described in (b) above has the amino acid sequence of SEQ ID NO: 1 in which one or several amino acid residues are substituted, deleted, inserted, and/or added (or, collectively, "mutation") as long as the glucose dehydrogenase activity is not impaired.

When the mutation is amino acid substitution, the type of amino acid substitution is not particularly limited, but is preferably a conservative amino acid substitution, because it does not cause a significant effect on the phenotype of FGDH. "Conservative amino acid substitution" refers to a replacement of an amino acid residue with another amino acid residue having a side chain with similar properties. Amino acid residues are grouped into various families according to their side chains, such as basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). Therefore, a replacement between amino acid residues of the same family is preferable.

One or more mutations can be performed by introducing one or more mutations into DNA encoding the CsGDH of the present invention (mentioned below) by using known techniques, such as restriction enzyme treatment, treatment with exonuclease, DNA ligase, or the like, a site-directed mutagenesis induction method, a random mutagenesis introduction method (*Molecular Cloning*, Third Edition, Chapter 13, Cold Spring Harbor Laboratory Press, New York), and the like. Other methods, such as ultraviolet irradiation, may also be used to produce variants. Variants encompass naturally occurring variants (e.g., single nucleotide polymorphism), based on, for example, individual variability of microorganisms carrying CsGDH, or on difference in species or families of those microorganisms.

In terms of maintaining the FGDH activity, the one or more mutations above preferably present in sites that do not influence the CsGDH active site or substrate binding site.

The polypeptide described in (c) above is a polypeptide having an amino acid sequence with 80% or more identity to the amino acid sequence of SEQ ID NO: 1 as long as the glucose dehydrogenase activity and preferably the characteristics described in Sections 1-3 to 1-9 below (in particular, Sections 1-3, 1-4, 1-8, and 1-9) are maintained. The amino acid sequence of the FGDH of the present invention preferably has 85% or more, more preferably 88% or more, still more preferably 90% or more, even more preferably 93% or more, further preferably 95% or more, particularly preferably 98% or more, and most preferably 99% or more, identity to the amino acid sequence of SEQ ID NO: 1. A polypeptide having an amino acid sequence with the certain degree of identity can be produced based on known genetic engineering techniques mentioned above.

In a preferred embodiment, the FGDH comprising an amino acid sequence having at least 80% identity to the sequence of SEQ ID NO: 1 does not comprise an amino acid sequence that is identical to the sequence of SEQ ID NO: because such an altered FGDH may possess an improved characteristic compared to the FGDH having the sequence of SEQ ID NO: 2.

In another preferred embodiment, the FGDH comprising an amino acid sequence having at least 80% identity to the sequence of SEQ ID NO: 1 is obtained by recombinantly expressing a DNA encoding the amino acid sequence having at least 80% identity to the sequence of SEQ ID NO:1. The FGDH obtained through a recombinant expression of a gene encoding of the FDGH is structurally different from the FGDH obtained from *Colletotrichum* RD056779, for example, with respect to sugar chains bound to the FGDH. The difference mainly results from the host cell used for the recombinant expression because the sugar chain pattern is unique to the host cell. In a preferred embodiment, the host cell may be different from *Colletotrichum* RD056779. The recombinant expression can be performed according to known methods, examples of which are discussed below.

Various methods are known for calculating amino acid sequence identity. For example, amino acid sequence identity can be calculated using a commercially available analytical tool or an analytical tool available through telecommunication lines (Internet).

In this specification, the online homology algorithm Basic Local Alignment Search Tool (BLAST program) of the U.S. National Center for Biotechnology Information (NCBI), available at http://www.ncbi.nlm.nih.gov/BLAST/, is used for the calculation of amino acid sequence identity using parameters with default (initial) settings.

1-3. Molecular Weight

The polypeptide moiety constituting the FGDH of the present invention has a molecular weight of about 65 kDa as measured by SDS-PAGE. "About 65 kDa" includes a range in which a person skilled in the art would usually determine that the band is present at a position of 65 kDa when a molecular weight is measured by SDS-PAGE. "Polypeptide moiety" refers to FGDH substantially not having an attached sugar chain. When the FGDH of the present invention produced by microorganisms is in a glycosylated form, heat treatment or glycohydrolase treatment may be performed so that the sugar chains are removed (i.e., so that the polypeptide moiety is obtained). The state of substantially not having an attached sugar chain allows the existence of sugar chains necessarily remaining after heat treatment or glycohydrolase treatment of the FGDH in a glycosylated form. Therefore, when FGDH is originally not in a glycosylated form, the FGDH itself corresponds to the polypeptide moiety.

Various methods are known for removing sugar chains from FGDH in a glycosylated form.

This specification uses a method comprising denaturing the FGDH in a glycosylated form by heat treatment at 100° C. for 10 minutes, followed by treatment at 37° C. for 6 hours with N-glycosidase Endo H (produced by New England Biolabs), as shown in the Examples below.

When the FGDH of the present invention has an attached sugar chain, its molecular weight is not limited as long as no adverse effect is made on the glucose dehydrogenase activity, substrate specificity, specific activity, or the like. For example, when the FGDH of the present invention has an attached sugar chain, the molecular weight is preferably 70 to 90 kDa as measured by SDS-PAGE. Considering that it better stabilizes the enzyme, and enhances water solubility to be easily dissolved in water, FGDH in a glycosylated form is preferable.

The molecular weight measurement by SDS-PAGE may be performed using general techniques and devices with the use of commercially available molecular weight markers.

1-4. Substrate Specificity

The FGDH of the present invention has excellent substrate specificity. In particular, the FGDH of the present invention has significantly reduced reactivity at least to D-xylose, compared to the reactivity to D-glucose. More specifically, the FGDH of the present invention has reactivity to D-xylose of preferably 2% or less, more preferably 1.0% or less, still more preferably 0.7% or less, and even more preferably 0.5% or less, based on the reactivity to D-glucose at the same concentration taken as 100%.

In addition to the low reactivity to D-xylose, it is preferable that the FGDH of the present invention also has low reactivity to D-galactose and maltose. The FGDH of the present invention has reactivity to D-galactose of preferably 2% or less, more preferably 1.0% or less, still more preferably 0.7% or less, even more preferably 0.5% or less, and still even more preferably 0.2% or less, based on the reactivity to D-glucose at the same concentration taken as 100%.

The FGDH of the present invention has reactivity to maltose of preferably 2% or less, more preferably 1.0% or less, still more preferably 0.7% or less, even more preferably 0.5% or less, and still even more preferably 0.3% or less, based on the reactivity to D-glucose at the same concentration taken as 100%.

In this specification, the reactivity of FGDH of the present invention to each sugar can be measured by replacing D-glucose with another sugar (e.g., D-xylose, D-galactose, or maltose) in the method for measuring the glucose dehydrogenase activity described in Section 1-1 above, and comparing the results with the results of the D-glucose activity. For comparison, the concentration of each sugar is 50 mM. Further, the substrate specificity is measured at a final enzyme concentration of the reaction liquid of 0.1 µg/mL when the reactivity to glucose is measured, and of 0.5 mg/mL when the reactivity to xylose, maltose, or galactose is measured.

The FGDH of the present invention having such excellent substrate specificity is preferably used as an enzyme for accurately measuring the amount of glucose in a sample. Specifically, the FGDH of the present invention can accurately measure the amount of target D-glucose even when the sample contains impurities, such as maltose, D-galactose, and D-xylose. Therefore, this enzyme of the present invention is considered to be suitable for applications where impurities in a sample are a concern or expected (typically, suitable for measuring the amount of glucose in blood). In addition to these applications, this enzyme is also applicable to various applications and is highly versatile.

1-5. Specific Activity

The FGDH of the present invention preferably has high specific activity in a purified preparation that has been purified to the extent that it migrates as a single band on electrophoresis (SDS-PAGE).

When the FGDH purified preparation is in a solid state (including powder), the solid weight is taken as the protein weight, and the enzyme activity is separately measured to calculate the specific activity. When the purified preparation is in a liquid state, the protein weight is measured using a protein quantification reagent produced by Bio-Rad Laboratories, Inc. (trade name: Bio-rad protein assay dye reagent concentrate) to calculate the specific activity.

To obtain the FGDH of the present invention as a purified preparation, purification is preferably performed to the extent that the specific activity is, for example, 30 or more (U/mg), more preferably 50 or more (U/mg), still more preferably 80 or more (U/mg), even more preferably 100 or more (U/mg), and still even more preferably 130 or more (U/mg). The upper limit of the specific activity is not limited, and is particularly preferably 200 or less (U/mg), more preferably 180 or less (U/mg), still more preferably 160 or less (U/mg), and even more preferably 150 or less (U/mg).

The final form of the purified preparation of the FGDH of the present invention may either be a liquid or a solid (including powder).

1-6. Optimum Activity pH

The FGDH of the present invention preferably has the highest activity at a pH of 7.0 (phosphate buffer solution), as shown in the Examples below. The FGDH of the present invention preferably has a relative activity of 80% or more at a pH of 6.5 to 8.0, based on the activity at a pH of 7.0 (phosphate buffer solution) taken as 100%. Specifically, the FGDH of the present invention has an optimal activity pH of 6.5 to 8.0, and preferably 7.0.

1-7. Optimal Activity Temperature

The FGDH of the present invention has an optimal activity temperature of preferably 30 to 55° C. The optimal activity temperature of 30 to 55° C. as used herein typically means that the temperature is more or less within a range of 30 to 55° C., and the range further includes an acceptable allowance to some extent. In this specification, the optimal activity temperature can be calculated by measuring the enzyme activity in potassium phosphate buffer solution (pH of 7.0) at a final enzyme concentration of the reaction liquid of 0.2 µg/mL, as shown in the Examples below.

1-8. pH Stability

In this specification, when 2 U/mL of enzyme that has been treated at 25° C. for 16 hours under specific pH conditions has remaining enzyme activity of 80% or more compared to the enzyme activity of the same enzyme before treatment, this enzyme is considered to be stable under these pH conditions. The FGDH of the present invention is preferably stable at least within the entire pH range of 3.5 to 10.0.

1-9. Temperature Stability

In this specification, when 2 U/mL of enzyme that has been treated for 15 minutes in an appropriate buffer solution (e.g., potassium acetate buffer (pH of 5.0)) under specific temperature conditions has remaining enzyme activity of 80% or more compared to the enzyme activity of the same enzyme before treatment, this enzyme is considered to be stable under these temperature conditions. The FGDH of the present invention is preferably stable at least at 55° C. or less (i.e., within a temperature range of 0 to 55° C.)

The FGDH of the present invention preferably has at least one or more, more preferably 2 or more, still more preferably 3 or more, even more preferably 4 or more, further preferably 5 or more, yet further preferably 6 or more, and particularly preferably all, of the characteristics described in Sections 1-3 to 1-9 above. The FGDH of the present invention may have any combination of the characteristics described in Sections 1-3 to 1-9 above. The FGDH of the present invention preferably has the characteristics described in Sections 1-3 and 1-4 above. The FGDH of the present invention more preferably has the characteristics described in Sections 1-5, 1-8, and 1-9, in addition to the characteristics described in Sections 1-3 and 1-4.

1-10. Origin

The origin of the FGDH of the present invention is not particularly limited as long as the FGDH has the characteristics described above. The FGDH of the present invention can be derived from, for example, microorganisms belonging to the genus *Colletotrichum* or the genus *Glomerella*, the sexual stage of *Colletotrichum*. The microorganisms belonging to the genus *Colletotrichum* are not particularly limited. Examples include *Colletotrichum acutatum*, *Colletotrichum boninense*, *Colletotrichum capsici*, *Colletotrichum circinans*, *Colletotrichum coccodes*, *Colletotrichum dematium*, *Colletotrichum falcatum*, *Colletotrichum gloeosporioides*, *Colletotrichum lindemuthianum*, *Colletotrichum musae*, *Colletotrichum orbiculare*, *Colletotrichum sasaecola*, *Colletotrichum trichellum*, *Colletotrichum trifolii*, and *Colletotrichum truncatum*. The microorganisms belonging to the genus *Glomerella* are not particularly limited. Examples include *Glomerella cingulata*, *Glomerella fructigena*, *Glomerella fusarioides*, *Glomerella glycines*, *Glomerella gossypii*, *Glomerella lagenaria*, *Glomerella tucumanensis*, and the like. More specific examples include *Colletotrichum* RD056779. *Colletotrichum* RD056779 is maintained in the international cooperation department of the National Institute of Technology and Evaluation (NITE) Biological Resource Center and can be obtained after completing predetermined procedures.

Examples of other organisms from which the FGDH of the present invention is derived include microorganisms living in soil, rivers, lakes, and other water systems; microorganisms living in oceans; microorganisms indigenously present in the surface of or inside various animals or plants, and the like. As an isolation source, it is also possible to use microorganisms that thrive in low-temperature environments; high-temperature environments such as volcanoes; anoxic, high-pressure, and aphotic environments such as deep seas; and special environments such as oil fields.

In addition to FGDH directly isolated from microorganisms, the FGDH of the present invention also includes FGDH obtained through protein engineering methods by which the amino acid sequence, etc., of isolated FGDH has been modified, or FGDH obtained through genetic engineering techniques by which the isolated FGDH has been modified. For example, it is possible to use enzymes that are isolated from, for example, microorganisms of the genus *Colletotrichum* or the genus *Glomerella*, which is the sexual stage of the genus *Colletotrichum*, and that are modified to have the characteristics described above.

2. DNA Encoding Flavin-Bound Glucose Dehydrogenase

The DNA of the present invention encodes the FGDH described in Section 1 above. Specifically, the DNA of the present invention is any one of the following (A) to (F):
(A) DNA encoding the amino acid sequence of SEQ ID NO: 1;
(B) DNA having the base sequence of SEQ ID NO: 2;
(C) DNA having a base sequence with 80% or more identity to the base sequence of SEQ ID NO: 2, and encoding a polypeptide having glucose dehydrogenase activity;
(D) DNA having a base sequence hybridizing to a base sequence complementary to the base sequence of SEQ ID NO: 2 under stringent conditions, the base sequence encoding a polypeptide having glucose dehydrogenase activity;
(E) DNA having the base sequence of SEQ ID NO: 2 in which one or several bases are substituted, deleted, inserted, added, and/or inverted, the base sequence encoding a polypeptide having glucose dehydrogenase activity; and
(F) DNA having a base sequence encoding the amino acid sequence of SEQ ID NO: 1 in which one or several amino acid residues are substituted, deleted, inserted, and/or added, the base sequence encoding a polypeptide having glucose dehydrogenase activity.

As used in this specification, the phrase "DNA encoding a protein (a polypeptide, FGDH, or the like) refers to DNA from which the protein is obtained when the DNA is expressed. Specifically, "DNA encoding a protein" refers to DNA having a base sequence corresponding to the amino acid sequence of the protein. Therefore, "DNA encoding a protein" also includes DNA that varies according to codon degeneracy.

The DNA of the present invention has a base sequence with 80% or more, preferably 85% or more, more preferably 88% or more, still more preferably 90% or more, even more preferably 93% or more, further preferably 95% or more, particularly preferably 98% or more, and most preferably 99% or more, identity to the base sequence of SEQ ID NO: 2 as long as the protein having the amino acid sequence encoded by this DNA has glucose dehydrogenase activity and preferably at least one characteristic from among the characteristics described in Sections 1-3 to 1-9 above (particularly one or more characteristics described in Sections 1-3, 1-4, 1-5, and 1-8).

In a preferred embodiment, the DNA comprising a base sequence that has at least 80%, 85%, 88%, 90%, 93%, 95%, 98%, or 99% identity to the sequence of SEQ ID NO: 2 and encodes a polypeptide having GDH activity does not comprise a base sequence identical to the sequence of SEQ ID NO: 2. Such an altered DNA may encode an FGDH with an improved characteristic compared to the alkaline phosphatase having the sequence of SEQ ID NO: 1. The altered DNA may also be preferred because the codon frequency of the DNA may be optimized with respect to the type of host cell within which the DNA is expressed.

Various methods are known for calculating the base sequence identity. For example, the base sequence identity can be calculated using a commercially available analytical tool or an analytical tool available through telecommunication lines (Internet). In this specification, the identity (%) of a base sequence is calculated using the homology algorithm Basic Local Alignment Search Tool (BLAST program) of the U.S. National Center for Biotechnology Information (NCBI) with default parameters (initial settings).

The DNA of the present invention may be DNA hybridizing to a base sequence complementary to the base sequence of SEQ ID NO: 2 under stringent conditions as long as the protein coded by this DNA has glucose dehydrogenation activity and preferably at least one characteristic from among characteristics described in Sections 1-3 to 1-9 above, and more preferably Sections 1-3, 1-4, 1-5, 1-8, and 1-9. "Stringent conditions" as used herein refers to conditions under which a specific hybrid is formed and a non-specific hybrid is not formed. Such stringent conditions would be known to a person skilled in the art and may be established with reference to, for example, *Molecular Cloning* (Third Edition, Cold Spring Harbor Laboratory Press, New York).

"Stringent conditions" as used in this specification refer to conditions in which a hybridization solution (50% formamide, 5×SSC (0.15 M NaCl, 15 mM sodium citrate, pH of 7.0), 1×Denhardt's solution, 1% SDS, 10% dextran sulfurate, 10 µg/mL of denatured salmon sperm DNA, and 50 mM phosphoric acid buffer (pH of 7.5)) is used.

DNA that undergoes hybridization under the above conditions possibly includes DNA containing a stop codon in the middle, or DNA whose activity is abolished as a result of the mutation in the active center. However, such DNA can be easily removed by introducing it into a commercially available active expression vector, expressing it in a suitable host, and determining the enzyme activity using known techniques.

In a preferable embodiment, DNA encoding the FGDH of the present invention is present in an isolated state. As used herein, DNA in an "isolated" state means that the DNA is separated from components such as other nucleic acids and proteins that coexist in nature. However, it is possible for the isolated DNA to contain a portion of other nucleic acid components, such as nucleic acid sequences (e.g., promoter region sequences and terminator sequences) that naturally flank the DNA sequence. For example, chromosomal DNA in an isolated state is preferably substantially free of other DNA components coexisting in nature. When DNA prepared by genetic engineering techniques, such as cDNA molecules, is in an isolated state, it is preferably substantially free of cell components, culture media, and the like. Likewise, when DNA prepared by chemical synthesis is in an isolated state, it is preferably substantially free of precursors (starting materials) such as dNTP, as well as chemical substances, etc., used in the synthetic process. When referred to simply as "DNA" in this specification, it means that the DNA is in an isolated state unless otherwise clearly stated that it has a different meaning. The DNA of the present invention also includes DNA (cDNA) complementary to the DNAs described in (A) to (F) above.

The DNA of the present invention may be produced or obtained by chemical DNA synthesis based on this specification or the sequence information (in particular SEQ ID NO: 2) in the accompanying Sequence Listing. For example, it is possible to easily prepare the DNA of the present invention by using standard genetic engineering techniques, molecular biological techniques, biochemical techniques, and the like (see, for example, *Molecular Cloning*, 3rd Ed., Cold Spring Harbor Lab. Press (2001)). Examples of chemical DNA synthesis include solid-phase synthesis using a phosphoramidite method. An automated synthesis device may be used in this synthesis.

Standard genetic engineering techniques can be performed, specifically, by preparing a cDNA library from suitable source microorganisms that can express the FGDH of the present invention according to a known method, and selecting desired clones using an appropriate probe or antibody specific to the DNA sequence of the present invention (e.g., the base sequence of SEQ ID No: 2) (see, for example, *Proc. Natl. Acad. Sci. USA.*, 78, 6613 (1981)).

The source microorganisms for preparing a cDNA library are not limited as long as they express the FGDH of the present invention, but are preferably microorganisms of the genus *Colletotrichum*, and more specifically, microorganisms stated in Section 1-10 above.

Separation of total RNA from the above microorganisms, separation and purification of mRNA, production and cloning of cDNA, and the like, may all be carried out using known methods. Methods for screening cDNA libraries for the DNA of the present invention are also not limited and can be performed using usual methods. For example, a method may be used in which an immunological screening is performed by using antibodies specific to a polypeptide derived from cDNA to select the corresponding cDNA clones. It is also possible to use a plaque hybridization method or a colony hybridization method using probes that selectively bind to the target nucleotide sequence. Combinations of these methods may also be used.

In obtaining DNA, it is preferable to use PCR or modified versions of PCR, such as DNA or RNA amplification methods. If obtaining full-length cDNA from libraries is difficult, it is preferable to use a RACE method, in particular, a 5'-RACE method (M. A. Frohman, et al., *Proc. Natl. Acad. Sci. U.S.A.*, 8, 8998 (1988)), or the like.

The primers used in PCR may also be suitably designed and synthesized based on the base sequence of SEQ ID NO: 2. As described above, amplified DNA or RNA fragments may be isolated and purified according to known methods, such as gel electrophoresis and hybridization.

The use of the DNA of the present invention enables easy and stable production of the FGDH of the present invention in large amount.

3. Vector

The vector of the present invention contains the DNA encoding the FGDH of the present invention described in Section 2 above. "Vector" as used herein is not particularly limited in terms of the type and the structure insofar as it is a nucleic acid molecule (carrier) that can transfer an inserted nucleic acid molecule to a target such as a cell, it can replicate the DNA of the present invention in a suitable host cell, and it can express the DNA of the present invention. Specifically, the vector of the present invention is an expression vector. An appropriate type of vector is selected in consideration of the type of host cell. Specific examples of vectors include plasmid vectors, cosmid vectors, phage vectors, viral vectors (e.g., adenoviral vectors, adeno-associated viral vectors, retroviral vectors, herpesviral vectors), and the like. Vectors suitably used when filamentous fungi are used as hosts may also be used. It is also possible to use vectors suitable for self-cloning.

In the use of *Escherichia coli* as a host, it is possible to use, for example, an M13 phage or modifications thereof, a λ phage or modifications thereof, pBR322 or modifications thereof (e.g., pB325, pAT153, pUC8), and the like. In the use of yeasts as hosts, pYepSec1, pMFa, pYES2, and the like, may be used. In the use of insect cells as hosts, for example, pAc and pVL may be used. In the use of mammalian cells as hosts, for example, pCDM8 and pMT2PC may be used. However, the vectors are not limited to these examples.

An expression vector usually contains, for example, a promoter sequence required for expression of inserted nucleic acid, and an enhancer sequence for facilitating the expression. It is also possible to use an expression vector containing a selection marker. In the use of such an expression vector, whether the expression vector is introduced (and the degree of the introduction) can be confirmed using the selection marker. Insertion of the DNA of the present invention into a vector, insertion of a selection marker gene (if required), insertion of a promoter (if required), and the like, may be performed using standard recombinant DNA technology (e.g., well-known methods that use restriction enzymes and DNA ligase, with reference to *Molecular Cloning*, Third Edition, 1.84, Cold Spring Harbor Laboratory Press, New York).

4. Transformant

The present invention also relates to a transformant obtained by introducing the DNA of the present invention into a host cell. The means for introducing the DNA of the present invention into a host cell is not particularly limited. For example, the DNA contained in a vector described in Section 3 above is introduced into a host cell. Host cells are not particularly limited as long as they can express the DNA of the present invention to produce FGDH. Specifically, it is possible to use prokaryotic cells, such as *Escherichia coli* and *Bacillus subtilis*; and eukaryotic cells, such as yeast, mold, insect cells, plant culture cells, and mammal cells. Examples of prokaryotic cells used as a host include the genera *Escherichia, Bacillus, Brevibacillus, Corynebacterium*, and the like. Examples of the genera include *Escherichia coli* C600, *Escherichia coli* HB101, *Escherichia coli* DH5α, *Bacillus subtilis, Brevibacillus choshinensis, Corynebacterium glutamicum*, and the like. Examples of the vectors include pBR322, pUC19, pBluescript, and the like. Examples of yeasts used as a host include the genera *Saccharomyces, Schizosaccharomyces, Candida, Pichia, Cryptococcus*, and the like. Examples of the genera include *Saccharomyces cerevisiae, Schizosaccharomyces pombe, Candida utilis, Pichia pastoris, Cryptococcus* sp., and the like. Examples of the vectors include pAUR101, pAUR224, pYE32, and the like. Examples of filamentous fungal cells used as a host include the genera *Aspergillus, Trichoderma, Colletotrichum*, and the like. Examples of the genera include *Aspergillus oryzae, Aspergillus niger, Trichoderma ressei, Colletotrichum hiemalis*, and the like.

As a host, it is also preferable in the present invention to use microorganisms that belong to the genus *Colletotrichum* from which the FGDH is isolated. Specifically, although in transformants, foreign DNA is generally present in a host cell, a preferable embodiment also includes transformants obtained by a self-cloning in which microorganisms from which the DNA is derived is used as a host.

The transformant of the present invention is preferably obtained by transfection or transformation of the expression vector described in Section 3 above. The transformation may be transient or stable transformation. Transfection or transformation may be performed by using a calcium phosphate co-sedimentation method, an electroporation method, a lipofection method, a microinjection method, a Hanahan method, a lithium acetate method, a protoplast-polyethylene glycol method, or the like.

The transformant of the present invention is capable of producing the FGDH of the present invention. Therefore, the use of the transformant of the present invention enables efficient production of the FGDH of the present invention.

5. Method for Producing Flavin-Bound Glucose Dehydrogenase

The FGDH of the present invention is produced by culturing microorganisms that are capable of producing the FGDH of the present invention. Microorganisms to be cultured are not particularly limited as long as they are capable of producing the FGDH of the present invention. For example, wild-type microorganisms belonging to the genus *Colletotrichum* mentioned in Section 1 above and the transformants described in Section 4 above are preferably used.

The microorganisms of the genus *Colletotrichum* are maintained, for example, in the international cooperation department of the NITE Biological Resource Center, and can be obtained after completing predetermined procedures.

The culture method and culture conditions are not limited as long as the FGDH of the present invention is produced. Specifically as long as FGDH is produced, any method and conditions can be used that are suitable for the growth of the microorganisms to be used. Examples of culture conditions, such as culture medium, culture temperature, and culture period, are described below.

There is no limitation on culture media as long as the microorganisms to be used can grow. Examples include those containing carbon sources, such as glucose, sucrose, gentiobiose, soluble starch, glycerin, dextrin, molasses, and organic acids; nitrogen sources, such as ammonium sulfate, ammonium carbonate, ammonium phosphate, ammonium acetate, peptone, yeast extract, corn steep liquor, casein hydrolysate, wheat bran, and meat extract; and inorganic salts, such as potassium salts, magnesium salts, sodium salts, phosphoric salts, manganese salts, iron salts, and zinc salts. To promote the growth of the microorganisms, it is also possible to add vitamins, amino acids, etc., to media.

When the FGDH of the present invention is obtained by culturing the microorganisms of the genus *Colletotrichum*, the culture conditions may be selected in consideration of nutritional and physiological properties of the microorganisms. Liquid culture is performed in many cases. Industrially, it is advantageous to perform aeration-agitation culture. In terms of the productivity, however, performing solid culture may be more advantageous.

The medium has a pH of, for example, about 3 to 8, and preferably about 5 to 7 as long as it is suitable for the growth of microorganisms to be cultured. Culture is performed at a culture temperature of usually about 10 to 50° C., preferably about 25 to 35° C., for 1 to 15 days, preferably about 3 to 7 days, under aerobic conditions. As a culture method, for example, shake culture or aerobic submerged culture using a jar fermentor may be used.

It is preferable that the FGDH is recovered from the culture medium or cells after culture under the above conditions. When microorganisms that secrete FGDH out of the cells are used, the enzyme of the present invention can be obtained, for example, in the following manner. Specifically, the culture supernatant is filtered, centrifuged, etc., to remove insoluble matter, and separation and purification are performed by suitably combining the following: ultrafiltration membrane concentration, ammonium sulfate precipitation and other salting out, dialysis, various chromatographies, and the like. A flavin-bound glucose dehydrogenase produced by microorganisms that belong to the genus *Colletotrichum* is basically a secretory protein.

In contrast, when the FGDH is recovered from inside the cells, the enzyme of the present invention can be obtained, for example, in the following manner. Specifically, the cells are disrupted by pressure treatment, ultrasonic treatment, mechanical technique, or techniques using enzymes such as lysozyme, and a surfactant and a chelating agent such as EDTA are optionally added to solubilize FGDH, which is separated and collected as an aqueous solution, followed by separation and purification. It is also possible to perform this series of processes (cell disruption, separation, and purification) after recovering cells in advance from culture medium by filtration, centrifugation, or the like.

Purification may be performed, for example, by suitably combining concentration such as vacuum concentration or membrane concentration; salting out with ammonium sulfate, sodium sulfate, or the like; fractional precipitation with a hydrophilic organic solvent such as methanol, ethanol, or acetone; heat treatment; isoelectric focusing; gel filtration with an adsorbent or a gel filtration agent; adsorption chromatography; ion-exchange chromatography; affinity chromatography; and the like.

When column chromatography is used, for example, gel-filtration column chromatography using Sephadex gel (produced by GE Healthcare Bioscience) and column chromatography using DEAF Sepharose CL-6B (produced by GE Healthcare Bioscience) or Octyl Sepharose CL-6B (produced by GE Healthcare Bioscience) may be used. It is preferable that the purified enzyme preparation be purified to the extent that the enzyme migrates as a single band on electrophoresis (SDS-PAGE).

In harvesting (e.g., extracting or purifying) a protein having glucose dehydrogenase activity from culture medium, any of the following may be used, singly or multiply, as indices: glucose dehydrogenase activity, reaction on maltose, thermal stability, and the like.

In each purification process, in principle, the GDH activity is used as an index for fractionation, thereby proceeding to the next step. This does not apply, however, if the appropriate conditions can be set in advance such as by performing a preliminary test.

To obtain the enzyme of the present invention as a recombinant protein, various modifications can be made. For example, DNA encoding the enzyme of the present invention and other appropriate DNA are inserted into the same vector, which is used to produce a recombinant protein. In this manner, the enzyme of the present invention made of a recombinant protein in which arbitrary peptides or proteins are linked together can be obtained. It is also possible to add sugar chains and/or lipid, or to make modifications that cause processing at the N-terminus or C-terminus. These modifications enable simplifying the extraction and purification of recombinant proteins, as well as addition of biological functions, and the like.

6. Method for Measuring Glucose

Methods for measuring glucose using glucose dehydrogenase have already been established in this technical field.

The amount or concentration of glucose in various samples can be measured using the FGDH of the present invention according to known methods. The mode for the measurement is not limited as long as the amount or concentration of glucose can be measured by using the FGDH of the present invention. For example, the measurement may be performed by causing the FGDH of the present invention to act on glucose in a sample, and spectrophotometrically measuring the structural change of the electron acceptor (e.g., DCPIP) associated with glucose dehydrogenation. More specifically, the measurement may be performed according to the method described in Section 1-1 above. According to the present invention, the glucose concentration can be measured by adding the FGDH of the present invention to a sample, or by adding the FGDH of the present invention to a sample, followed by mixing. The sample containing glucose is not limited. Examples of the samples include blood, beverages, foods, and the like. The amount of enzyme added to a sample is not limited as long as it is possible to measure the amount or concentration of glucose.

The glucose concentration can be measured using a sensor described later, for example, in the following manner. A buffer solution is placed in a thermostated cell, and the temperature is maintained constant. Potassium ferricyanide, phenazine methosulfate, or the like, can be used as a mediator. An electrode on which the FGDH of the present invention is immobilized is used as a working electrode, and a counter electrode (e.g., platinum electrode) and a reference electrode (e.g., Ag/AgCl electrode) are used. A constant voltage is applied across the carbon electrode. After the current becomes constant, a sample containing glucose is added, and the increase in current is measured. The glucose concentration in the sample can be calculated based on the calibration curve prepared from glucose solutions of standard concentration.

7. Glucose Assay Kit

The glucose assay kit of the present invention contains the FGDH of the present invention in an amount sufficient for at least one assay. In addition to the FGDH of the present invention, the kit typically contains a buffer solution and a mediator required for the assay, a glucose standard solution for preparing a calibration curve, and instructions for use. The FGDH of the present invention may be provided in various forms, such as a freeze-dried reagent or a solution in an appropriate storage solution.

8. Glucose Sensor

The present invention also provides a glucose sensor that uses the FGDH of the present invention. The glucose sensor of the present invention can be produced by immobilizing the enzyme of the present invention on an electrode, such as a carbon electrode, a gold electrode, or a platinum electrode. Examples of methods for immobilization include a method using a crosslinking reagent, a method for encapsulating the FGDH in a polymer matrix, a method for covering the FGDH with a dialysis membrane, and methods using a photo-crosslinkable polymer, a conductive polymer, a redox polymer, or the like. Alternatively, the FGDH of the present invention may be immobilized in a polymer or immobilized adsorptively onto an electrode, together with an electron mediator, such as ferrocene or its derivatives. These methods may also be used in combination. Since the FGDH of the present invention has excellent thermal stability, immobilization may be performed at a relatively high temperature (e.g., 50° C. or 55° C.) Typically, the FGDH of the present invention is immobilized on a carbon electrode using glutaraldehyde, followed by treatment with an amine-containing reagent. In this manner, the glutaraldehyde can be blocked.

The glucose concentration can be measured using a sensor in the following manner. A buffer solution is placed in a thermostated cell, and the temperature is maintained constant. Potassium ferricyanide, phenazine methosulfate, or the like, can be used as a mediator. An electrode on which the FGDH of the present invention is immobilized is used as a working electrode, and a counter electrode (e.g., platinum electrode) and a reference electrode (e.g., Ag/AgCl electrode) are used. A constant voltage is applied across the carbon electrode. After the current becomes constant, a sample containing glucose is added, and the increase in current is measured. The glucose concentration in the sample can be calculated based on the calibration curve prepared from glucose solutions of standard concentration.

The present invention is more specifically described below by presenting Examples. The descriptions of the Examples below are not intended to limit the present invention in any aspects.

EXAMPLES

Example 1

Reconstitution of Strain

Strains that belong to the genus *Colletotricum* were obtained from the international cooperation department of the National Institute of Technology and Evaluation (NITE) Biological Resource Center. The strains were reconstituted by being statically cultured at 25° C. for 3 to 7 days. DP medium (dextrin 2.0%, polypeptone 1.0%, $KH_2PO_4$ 1.0%, agarose 1.5%) was used as reconstitution medium.

Example 2

A loopful of each strain of the genus *Colletotricum* reconstituted in Example 1 was inoculated in a solid medium containing 2 g of wheat germ and 2 mL of 2% glucose solution sterilized in an autoclave at 120° C. for 20 minutes, and was statically cultured at 25° C. for about 5 to 7 days. After the culture, 1 mL of 50 mM potassium phosphate buffer solution (pH of 6.5) was added, and the cells were sufficiently suspended by vortex mixing. After a small amount of glass beads were added to the suspension, the cells were disrupted using a beads shocker (Yasui Kikai Corporation) at 3,000 rpm for 3 minutes, twice, followed by centrifugation for 5 minutes at 4° C., 2,000×g. The resulting supernatant was used as a crude enzyme solution.

Example 3

Confirmation of Glucose Dehydrogenase Activity

The activity of glucose dehydrogenase in the crude enzyme solution obtained in Example 2 was measured according to the glucose dehydrogenase measurement method shown in Section 1-1 above. Table 1 shows the results.

TABLE 1

| Strain | Activity (U/ml) |
|---|---|
| *Colletotrichum* (RD056779) | 0.38 |

As shown in Table 1, GDH activity was confirmed in the crude enzyme solution from *Colletotrichum* RD056779.

Example 4

Purification of GDH from *Colletotrichum* RD056779

50 mL of YPD medium (0.5% yeast extract, 1% peptone, and 2% glucose) was placed in a 500-mL Sakaguchi flask and sterilized in an autoclave, thereby preparing a preculture medium. A loopful of *Colletotrichum* RD056779 reconstituted in advance in DP plate medium was inoculated in the preculture medium and subjected to shaking culture for 5 days at 25° C., 180 rpm, thereby obtaining a seed culture solution.

Next, 6.0 L of a production medium (yeast extract 3.0%, glycerol 3.0%, pH of 6.0) was placed in a 10-L jar fermenter and sterilized in an autoclave, thereby obtaining a main culture medium. 50 mL of the seed culture solution was inoculated in the main culture medium and was cultured for 5 days under the following conditions: culture temperature=25° C., stirring speed=400 rpm, air flow rate=2.0 L/min, and tube internal pressure=0.2 MPa. Thereafter, the culture solution was filtrated, and the filtrate was concentrated using a UF membrane (Millipore) having a molecular weight cutoff of 30,000, and 50 mM phosphate buffer solution (pH of 6.0) was added to the concentrated solution. This step was repeated to remove low-molecular substances.

Subsequently, ammonium sulfate was gradually added to the desalinated solution to give 0.4 saturation, and the resulting liquid was subjected to linear gradient elution with 50 mM phosphate buffer solution (pH of 6.0) by being passed through a 400-mL PS Sepharose Fast Flow column (GE Healthcare) equilibrated in advance with 50 mM potassium phosphate buffer solution (pH of 6.0) containing 0.4-saturated ammonium sulfate. Thereafter, the eluted GDH fraction was concentrated using a hollow fiber membrane (Spectrum Laboratories, Inc.) having a molecular weight cutoff of 10,000, and was subjected to linear gradient elution with 50 mM phosphate buffer solution (pH of 6.0) containing 0.5 M NaCl by being passed through a DEAF Sepharose Fast Flow column (GE Healthcare) equilibrated with 50 mM potassium phosphate buffer solution (pH of 6.0), and then through a 5-mL Resource Phe column (GE Healthcare) equilibrated with 50 mM potassium phosphate buffer solution (pH of 6.0) containing 0.4-saturated ammonium sulfate, thereby obtaining a purified enzyme. The resulting purified enzyme was subjected to SDS-polyacrylamide gel electrophoresis (PhastGel 10-15% PhastSystem: GE Healthcare). Phosphorylase b (97,400 Da), bovine blood serum albumin (66,267 Da), aldolase (42,400 Da), carbonic anhydrase (30,000 Da), and trypsin inhibitor (20,100 Da) were used as protein molecular weight markers.

The obtained single band showed that GDH was sufficiently purified. Further, the mobility compared with the molecular weight markers showed that the molecular weight of the purified GDH was 78,000 to 90,000 Da.

Example 5

Confirmation of Flavin-Bound Enzyme

The enzyme purified in Example 4 was dialyzed with 50 mM phosphate buffer solution (pH of 7.0), and the absorption spectrum at 300 to 600 nm was measured using a spectrophotometer U-3210 (Hitachi High-Technologies Corporation). The results revealed that the enzyme had two peaks (maximum absorption wavelength) approximately at a wavelength of 380 to 390 nm and approximately at a wavelength of 450 to 470 nm (FIG. 1). The shape of the absorption spectrum strongly suggested that the GDH of the present invention is a flavin-bound protein (i.e., FGDH). (The GDH is hereinafter also referred to as "CsGDH.")

Example 6

Molecular Weight of Peptide Moiety of Isolated CsGDH

Figure 2:
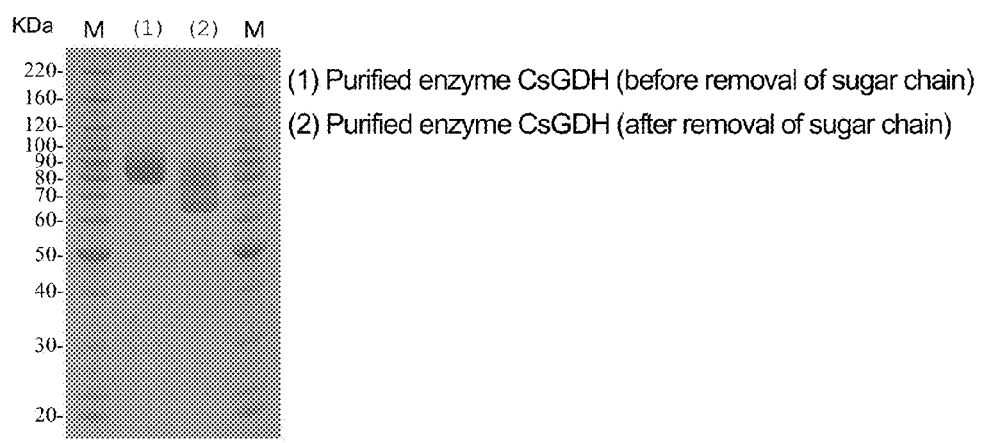
FIG. 2 shows the SDS-PAGE results of RD056779-derived GDH.

The purified CsGDH obtained in Example 4 was denatured by heating at 100° C. for 10 minutes, and then treated with 5 U of Endo H (New England Biolabs Inc.) at 37° C. for an hour, thereby decomposing the sugar chain added to the protein. Thereafter, the same measurement as in Example 4 was performed using SDS-polyacrylamide gels electrophoresis. The same molecular weight markers as in Example 4 were used. The results revealed that the molecular weight of the polypeptide moiety of the purified CsGDH was about 65,000 Da. FIG. 2 shows the results of the electrophoresis.

Example 6

Substrate Specificity

According to the GDH activity measurement method described in Section 1-1 above, the activity of the GDH purified in Example 4 was measured with respect to D-glucose, maltose, D-galactose, and D-xylose as substrates. Further, the activities with respect to other sugars relative to the activity (100%) with respect to D-glucose were found. The concentration of each sugar was 50 mM. Table 2 shows the results. The final enzyme concentration was 0.1 µg/ml for glucose, and 0.5 mg/ml for other sugars. The following enzyme activity measurement conditions were used in the present example.

1.79 mL of 100 mM phosphate buffer (pH of 7.0), 0.08 mL of 1.25M D-glucose solution, and 0.01 mL of 20 mM DCPIP solution were mixed, and the mixture was kept warm at a temperature of 37° C. for 5 minutes. Then, 0.02 mL of 20 mM PMS solution and 0.1 mL of enzyme sample solution were added to start the reaction. The absorbency at the beginning of the reaction and the absorbency over time were measured, and the decrement amount ($\Delta A600$) of the absorbency per minute at 600 nm with the advance of the enzyme reaction was found, thereby calculating the activity of flavin-bound GDH according to the formula below. The activity of the flavin-bound GDH is defined by determining the enzyme amount for reducing 1 µmol DCPIP for 1 minute at 37° C. in the presence of D-glucose having a concentration of 50 mM as 1 U.

$$\text{Activity (U/mL)} = \{-(\Delta OD_{TEST} - \Delta OD_{BLANK}) \times 2.0 \times \text{dilution factor}\}/\{16.3 \times 0.1 \times 1.0\}$$

In the formula, 2.0 is the liquid amount (mL) of the reaction reagent+enzyme reagent, and 16.3 is the mmol absorption coefficient ($cm^2$/µmol) under the present activity measurement conditions, 0.1 is a liquid amount (mL) of enzyme solution, 1.0 is the optical light path (cm) of the cell, and $\Delta OD_{BLANK}$ is the decrement amount of the absorbency per minute at 600 nm when the reaction was started by adding 10 mM acetic acid buffer solution instead of enzyme sample solution.

TABLE 2

| Sugar | Relative activities (%) |
|---|---|
| D-Glucose | 100.0 |
| Maltose | 0.3% or less |
| D-Galactose | 0.2% or less |
| D-Xylose | 0.5% or less |

The results of Table 2 revealed that the apparent activity of the purified CsGDH with respect to maltose, D-galactose, and D-xylose was 0.3% or less, 0.2% or less, and 0.5% or less, respectively, relative to its activity with respect to D-glucose (100%). It was thus shown that the CsGDH of the present invention has excellent substrate specificity.

Example 7

Optimal Activity pH

Figure 3:
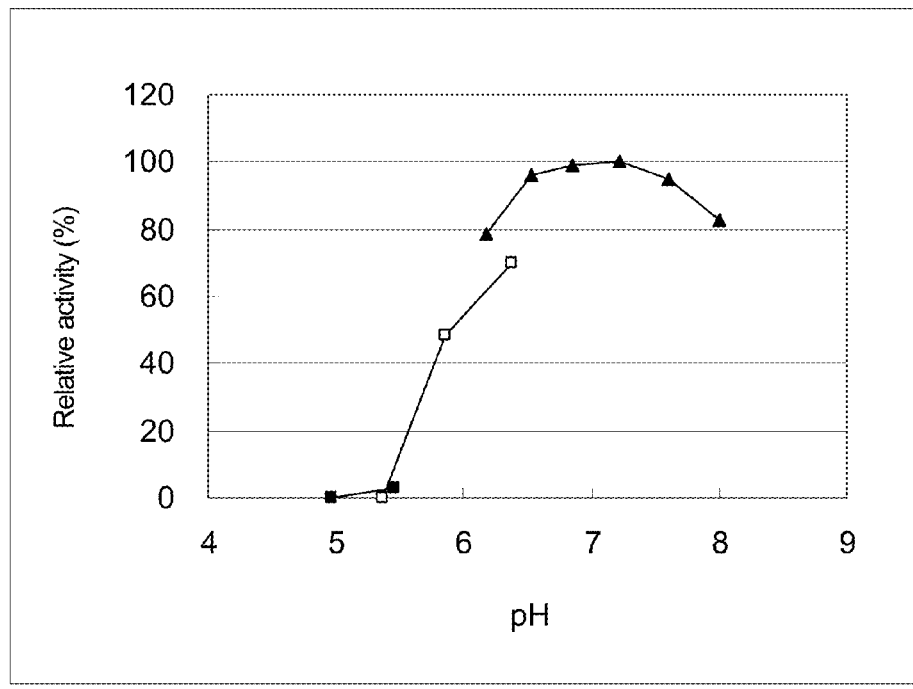
FIG. 3 is a graph showing the influence of pH on the activity of RD056779-derived GDH.

The optimal pH was found using the purified CsGDH enzyme liquid (0.5 U/mL) obtained in Example 4. An enzyme reaction was performed at 37° C. and different pH values using 100 mM acetic acid-potassium buffer solution (pH of 5.0 to 5.5, plotted with black squares in the figure), 100 mM MES-NaOH buffer solution (pH of 5.5 to 6.5, plotted with white squares in the figure), and 100 mM phosphoric acid-potassium buffer solution (pH of 6.0 to 8.0, plotted with black triangles in the figure) so as to compare the relative activities. FIG. 3 shows the results.

The results revealed that the optimal activity pH of the purified CsGDH was the highest at a pH of 7.0 when a phosphoric acid-potassium buffer solution was used. Further, the CsGDH showed a relative activity of 80% or more in a pH range of 6.5 to 8.0, based on the activity at a pH of 7.0 taken as 100%. These results showed that the optimal activity pH of the purified CsGDH falls within a range of about 6.5 to 8.0.

Example 8

Optimal Activity Temperature

Figure 4:
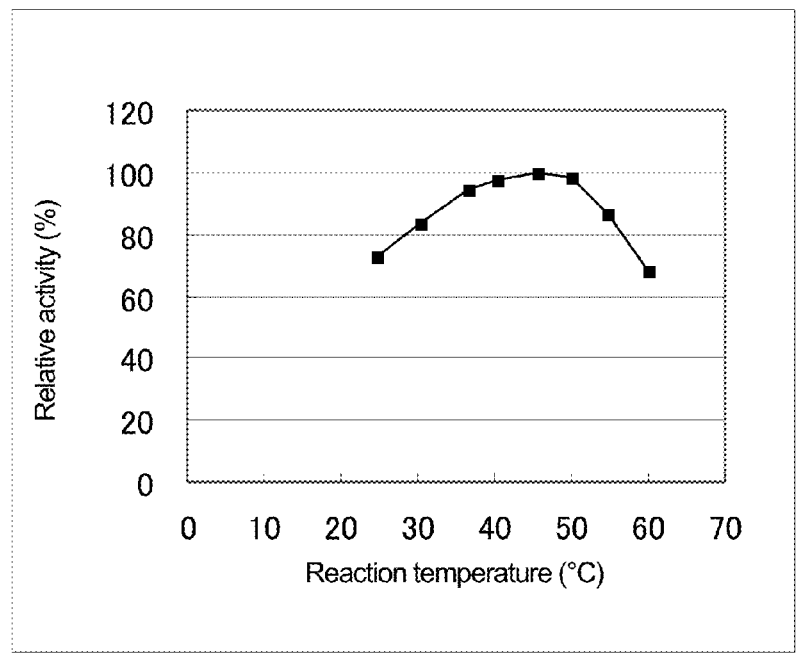
FIG. 4 is a graph showing the influence of temperature on the activity of RD056779-derived GDH.

The optimal activity temperature was found using the purified CsGDH enzyme liquid (3.5 µg/ml) obtained in Example 4. The activities at 25° C., 30° C., 37° C., 40° C., 46° C., 49° C., 50° C., 55° C., and 60° C. were measured. FIG. 4 shows the results. Further, the present example was measured under the following enzyme activity measurement conditions.

1.79 mL of 100 mM phosphate buffer solution (pH of 7.0), 0.08 mL of 1.25 M D-glucose solution, and 0.01 mL of 20 mM DCPIP solution were mixed and the mixture was kept at a temperature of 37° C. for 5 minutes. Then, 0.02 mL of 20 mM PMS solution and 0.1 mL of enzyme sample solution were added to start the reaction. The absorbency at the beginning of the reaction and the absorbency over time were measured, and the decrement amount (ΔA600) of the absorbency per minute at 600 nm with the advance of the enzyme reaction was found, thereby calculating the activity of flavin-bound GDH according to the formula below. The activity of the flavin-bound GDH is defined by determining the enzyme amount for reducing 1 µmol DCPIP for 1 minute at 37° C. in the presence of D-glucose having a concentration of 50 mM as 1 U.

$$\text{Activity (U/mL)} = \{-(\Delta OD_{TEST} - \Delta OD_{BLANK}) \times 2.0 \times \text{dilution factor}\} / \{16.3 \times 0.1 \times 1.0\}$$

In the formula, 2.0 is the liquid amount (mL) of the reaction reagent+enzyme reagent, and 16.3 is the mmol absorption coefficient (cm$^2$/µmol) under the present activity measurement conditions, 0.1 is a liquid amount (mL) of enzyme solution, 1.0 is the optical light path (cm) of the cell, and $\Delta OD_{BLANK}$ is the decrement amount of the absorbency per minute at 600 nm when the reaction was started by adding 10 mM acetic acid buffer solution instead of enzyme sample solution.

The results revealed that the activity value of the purified CsGDH was the highest at a temperature of 46° C. to 49° C., and the CsGDH showed a relative activity of 80% or more in a temperature range of 46° C. to 58° C., based on the highest activity. These results showed that the optimal activity temperature of the purified CsGDH falls within a range of 46° C. to 58° C.

Example 9 pH Stability

Figure 5:
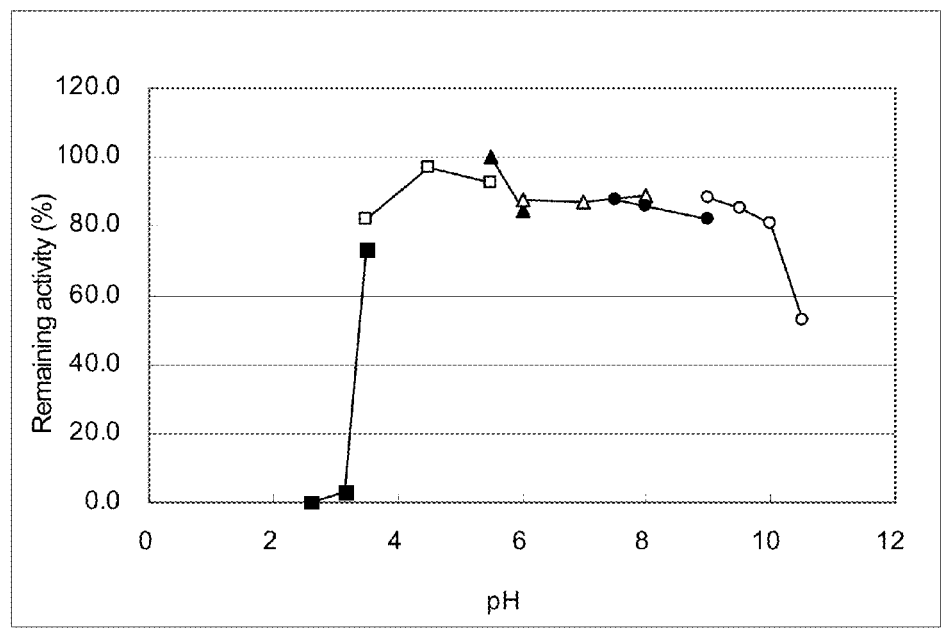
FIG. 5 is a graph showing the measurement results of the pH stability of RD056779-derived GDH.

The pH stability was measured using the CsGDH enzyme liquid (2 U/mL) obtained in Example 4. The activity was measured after the enzyme was retained in 100 mM glycine-HCl buffer solution (pH of 2.5 to 3.5, plotted with black squares in the figure), 100 mM acetic acid-potassium buffer solution (pH of 3.0 to 5.5, plotted with white squares in the figure), 100 mM MES-NaOH buffer solution (pH of 5.5 to 6.5, plotted with black triangles in the figure), and 100 mM potassium phosphate buffer solution (pH of 6.0 to 8.0, plotted with white triangles in the figure), 100 mM Tris-HCl buffer solution (pH of 7.5 to 9.0, plotted with black circles in the figure), and 100 mM glycine-NaOH buffer solution (pH of 9.0 to 10.5, plotted with white circles in the figure) with respect to glucose as the substrate for 16 hours at 25° C. The activity before the treatment and the activity after the treatment were compared to find the remaining activity. FIG. 5 shows the results.

The results revealed that the pH value at which the remaining activity of the purified CsGDH was 80% or more was a pH of 3.5 to 10.0. This shows that the stable pH range of the purified CsGDH is 3.5 to 10.0.

Example 10

Temperature Stability

Figure 6:
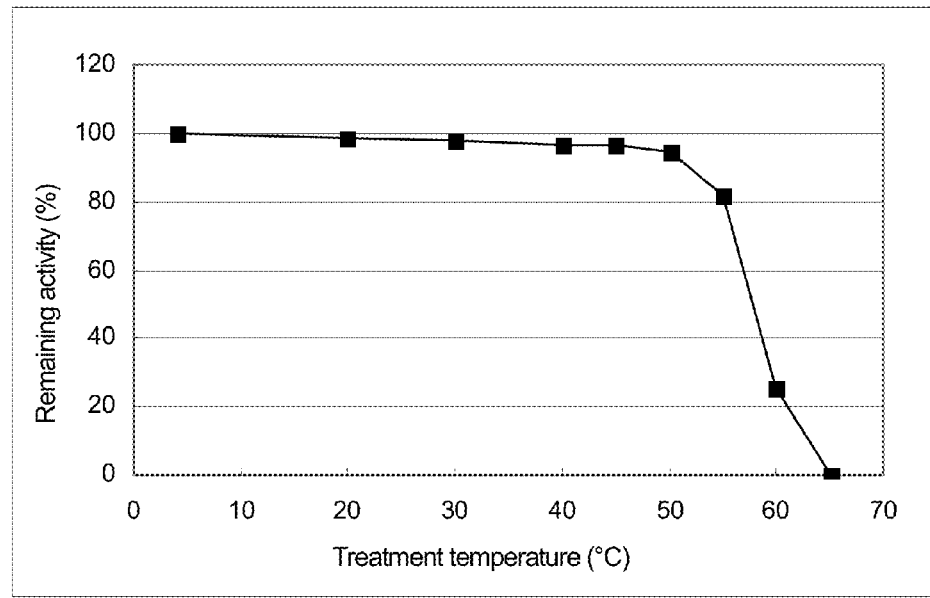
FIG. 6 is a graph showing the measurement results of the temperature stability of RD056779-derived GDH.
Figure 7:
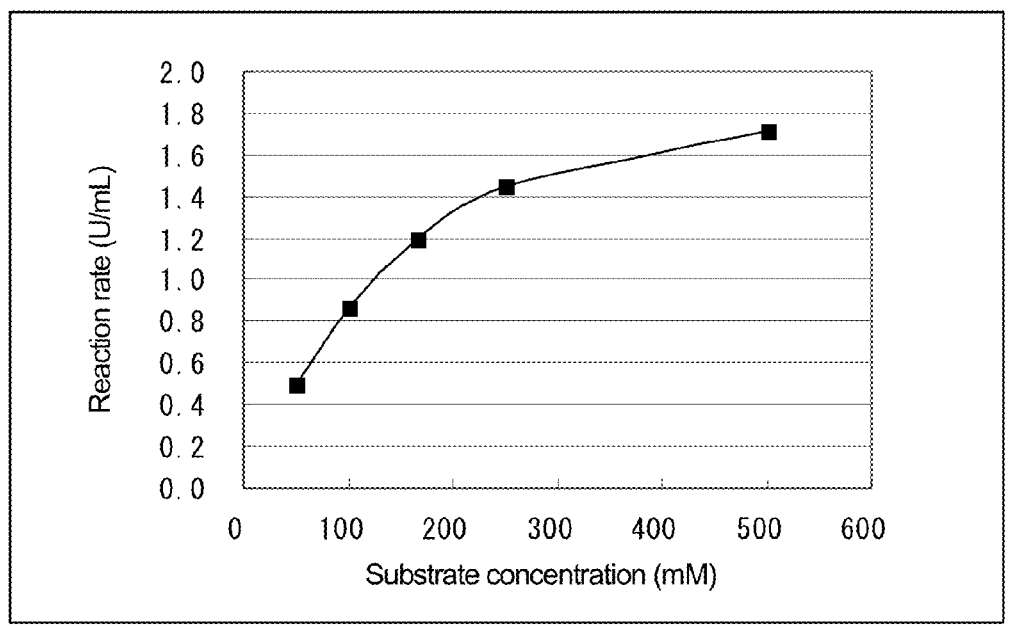
FIG. 7 is a graph showing the relationship between the reaction rate and substrate concentration of RD056779-derived GDH.

The temperature stability was measured using the purified CsGDH enzyme liquid (2 U/mL) obtained in Example 4. The CsGDH enzyme liquid was treated with 100 mM potassium acetate buffer solution (pH of 5.0) for 15 minutes at different temperatures (4° C., 30° C., 40° C., 50° C., 55° C., 60° C., 65° C., and 70° C.); thereafter, the GDH activity before the treatment and the GDH activity after the treatment were compared to find the remaining activity. FIG. 6 shows the results.

The results revealed that the remaining activity of the purified CsGDH was 80% or more after the treatment at a temperature in a range of 4° C. to 55° C. This shows that the stable temperature range of the purified CsGDH is 55° C. or less.

Further, FIG. 6 shows that the remaining activity of the purified CsGDH was 90% or more after the treatment at a temperature in a range of 4° C. to 50° C. This shows that the purified CsGDH is significantly stable at a temperature of 50° C. or less.

Example 11

Measurement of Specific Activity

The glucose dehydrogenase activity was measured using the purified CsGDH enzyme liquid (7 µg/mL) obtained in Example 4 by a method using only DCPIP as an electron acceptor. The measurement found the specific activity as 138 (U/mg). The mutant enzyme (double mutant of D446H and V582P) of the glucose oxidase from *Aspergillus niger* disclosed in patent document WO2011/068050A1 is superior in substrate specificity like the present invention. As disclosed in this patent document, expression in *Saccharomyces cerevisiae* and various types of chromatography were performed to prepare the enzyme. The glucose dehydrogenase activity was measured under the same conditions as above, with the result that the specific activity was 27 (U/mg). It was thus confirmed that the CsGDH of the present invention is superior in terms of not only substrate specificity but also specific activity.

Example 12

Cloning of *Colletotricum*-Derived Flavin-Bound GDH Gene and Expression Using Transformant (1) Preparation of Total RNA

*Colletotricum* RD056779 strain were inoculated into 60 mL of GDH production medium (yeast extract 3.0%, glycerol 3.0%, pH of 6.0) and subjected to shaking culture for 5 days at 25° C. The resulting culture solution was filtrated with filter paper, thereby recovering the mycelia. The resulting mycelia were frozen in liquid nitrogen and pulverized using a mortar. Then, total RNA was obtained from the pulverized cells using the hot phenol method.

(2) Determination of Amino Acid Sequence of GDH Moiety

The purified CsGDH obtained in Example 4 was subjected to SDS-polyacrylamide gel electrophoresis using Nu-PAGE 4-12% Bis-Tris Gel (Invitrogen Corporation). The gel after the electrophoresis was stained using Simply Blue Safe Stain (Invitrogen Corporation), and the portion of the band corresponding to the molecular weight of the enzyme was cut and separated. The cut gel fragment was sent to an external agency to obtain the internal amino acid sequence information in the protein. The obtained amino acid sequences were KGTADWSWDGILPFFKK (SEQ ID NO: 3) and KYDASYWGDSSEIYAGWPR (SEQ ID NO: 4).

(3) Determination of GDH Gene Sequence

With reference to the partial amino acid sequence obtained above, degenerate primers containing mixed bases were synthesized. (Examples of the primers are shown in SEQ ID NO: 5 (forward primer) and SEQ ID NO: 6 (reverse primer).) In SEQ ID NOS: 5 and 6, the single letters, which express mixed bases, mean the following: h=a+c+t, r=a+g, y=c+t, and d=a+g+t. Using the total RNA of *Colletotrichum* RD056779 strain prepared in Section (1) above as a template, RT-PCR was performed using a Smarter RACE cDNA Amplification kit (Clontech Laboratories, Inc.) in accordance with the protocol of the kit. The degenerate primers SEQ ID NOS: 5 and 6 were used for the cDNA amplification by PCR. The reaction liquid was subjected to agarose gel electrophoresis, and a single band having a length of approximately 100 bp was confirmed. The amplified DNA fragment in the band was purified, and the amplified DNA fragment was ligated to pTA2 (Toyobo Co., Ltd.) using Target Clone—Plus—(Toyobo Co., Ltd.), thereby constructing a recombinant plasmid pTA-056779GDH partial.

Then, with the resulting partial pTA-056779GDH partial, *Escherichia coli* DH5α competent cell (Toyobo Co., Ltd.) was transformed using a known heat shock method. A plasmid was extracted from the resulting transformant using MagExtractor—Plasmid—(Toyobo Co., Ltd.) and was purified. The base sequence of the amplified DNA fragment in the plasmid was determined (111 bp).

With reference to the sequence information of the amplified DNA fragment obtained above, unidentified regions of GDH gene at the 3' end and the 5' end were determined using a Smarter RACE cDNA Amplification kit (Clontech Laboratories, Inc.). According to the protocol of each kit, in the 3' RACE procedure, first PCR was performed using the primer of SEQ ID NO: 7 and the Universal Primer A Mix contained in the kit, and then nested PCR was performed using the primer of SEQ ID NO: 8 and the Nested Universal Primer A contained in the kit and; in the 5' RACE procedure, first PCR was performed using the primer of SEQ ID NO: 9 and the Universal Primer A Mix contained in the kit, and then nested PCR was performed using the primer of SEQ ID NO: 10 and the Nested Universal Primer A contained in the kit. As a result of the analysis of the base sequence of the DNA fragment contained in the obtained multiple plasmids, *Colletotrichum*-derived GDH gene sequence shown in SEQ ID NO: 2 having a total chain length of 1908 bp was identified. SEQ ID NO: 1 shows the amino acid sequence of the enzyme gene estimated from the gene sequence.

This invention is not limited to the above Embodiments and Examples. The invention also includes variations and modifications within the scope of the patent claims set forth below and within a range readily conceived of by those skilled in the art.

The entire content of papers, laid-open patent applications, and patent publications referred to in this specification is incorporated herein by reference.

INDUSTRIAL APPLICABILITY

The CsGDH of the present invention has excellent substrate specificity and enables more accurate measurement of the amount of glucose. The CsGDH of the present invention is thus suitable, for example, for measuring blood glucose levels.

---

The invention claimed is:

1. A glucose sensor comprising
   (a) an electrode and
   (b) a polypeptide comprising an amino acid sequence having more than 93% identity to the sequence of SEQ ID NO: 1 and having glucose dehydrogenase activity, wherein the polypeptide is immobilized on the electrode.

2. The glucose sensor of claim 1, wherein the amino acid sequence has at least 95% identity to the sequence of SEQ ID NO: 1.

3. The glucose sensor of claim 1, wherein the amino acid sequence has at least 98% identity to the sequence of SEQ ID NO: 1.

4. The glucose sensor of claim 1, wherein the amino acid sequence has at least 99% identity to the sequence of SEQ ID NO: 1.

5. The glucose sensor of claim 1, wherein the electrode is a platinum electrode, a silver electrode, or a carbon electrode.

6. An electrode comprising a polypeptide comprising an amino acid sequence having more than 93% identity to the sequence of SEQ ID NO: 1 and having glucose dehydrogenase activity, wherein the polypeptide is immobilized onto the electrode.

7. The electrode of claim 6, wherein the amino acid sequence has at least 95% identity to the sequence of SEQ ID NO: 1.

8. The electrode of claim 6, wherein the amino acid sequence has at least 98% identity to the sequence of SEQ ID NO: 1.

9. The electrode of claim 6, wherein the amino acid sequence has at least 99% identity to the sequence of SEQ ID NO: 1.

10. The electrode of claim 6, wherein the electrode is a platinum electrode, a silver electrode, or a carbon electrode.

11. A kit for glucose assay comprising
  (a) a mediator, wherein the mediator is an electron acceptor, and
  (b) a polypeptide comprising an amino acid sequence having more than 93% identity to the sequence of SEQ ID NO: 1 and having glucose dehydrogenase activity.

12. The kit of claim 11, wherein the amino acid sequence has at least 95% identity to the sequence of SEQ ID NO: 1.

13. The kit of claim 11, wherein the amino acid sequence has at least 98% identity to the sequence of SEQ ID NO: 1.

14. The kit of claim 11, wherein the amino acid sequence has at least 99% identity to the sequence of SEQ ID NO: 1.

15. The kit of claim 11, wherein the mediator is at least one selected from the group consisting of potassium ferricyanide and phenazine methosulfate.

16. The glucose sensor of claim 1, wherein the polypeptide is immobilized on the electrode by encapsulating the polypeptide in a polymer matrix.

17. The glucose sensor of claim 1, wherein the polypeptide is immobilized on the electrode by covering the polypeptide with a dialysis membrane.

\* \* \* \* \*